(12) United States Patent
Aneja et al.

(10) Patent No.: US 7,863,028 B2
(45) Date of Patent: Jan. 4, 2011

(54) METHODS AND DEVICE FOR PRODUCING HYDROGEN FROM BIOMASS

(75) Inventors: Karan Aneja, Los Angeles, CA (US); Siddhartha Saha, Berkeley, CA (US)

(73) Assignee: Sidkar Technologies, Inc., Los Angeles, CA (US)

( * ) Notice: Subject to any disclaimer, the term of this patent is extended or adjusted under 35 U.S.C. 154(b) by 597 days.

(21) Appl. No.: 11/874,499

(22) Filed: Oct. 18, 2007

(65) Prior Publication Data

US 2009/0087891 A1    Apr. 2, 2009

Related U.S. Application Data

(60) Provisional application No. 60/975,760, filed on Sep. 27, 2007.

(51) Int. Cl.
*C12P 3/00* (2006.01)
(52) U.S. Cl. .................................................. 435/168
(58) Field of Classification Search .................. None
See application file for complete search history.

(56) References Cited

U.S. PATENT DOCUMENTS 7,140,187 B2 * 11/2006 Amendola .................... 60/780

* cited by examiner

*Primary Examiner*—Herbert J. Lilling
(74) *Attorney, Agent, or Firm*—Hudak, Shunk & Farine Co. LPA

(57) ABSTRACT

Disclosed herein are methods of producing molecular hydrogen, where the methods comprise contacting a solution comprising urea with a urease to produce ammonia, and contacting the ammonia with a first catalyst to produce a first gaseous mixture comprising molecular hydrogen.

17 Claims, 1 Drawing Sheet

METHODS AND DEVICE FOR PRODUCING HYDROGEN FROM BIOMASS

RELATED APPLICATIONS

This application claims priority to the U.S. Provisional Application Ser. No. 60/975,760, filed on Sep. 27, 2007, by Aneja et al., and entitled "METHODS OF PRODUCING HYDROGEN FROM BIOMASS", the entire disclosure of which, including any drawings, is hereby incorporated by reference herein.

FIELD OF THE INVENTION

The present invention is in the field of alternative and clean fuels, and particularly in the field of producing and using hydrogen gas as fuel. In addition, the present invention is in the field of generation of hydrogen from biomass using enzymes and metal catalysts.

BACKGROUND OF THE DISCLOSURE

Molecular hydrogen is a very attractive environmentally friendly fuel. It reacts with oxygen in a highly exothermic reaction having a relatively low activation barrier. The by-product of this oxidation reaction is water. The use of hydrogen does not produce so-called green house gas by-products. Hydrogen currently is being used as fuel for propelling the space shuttle into orbit.

Despite the many advantages of the use of hydrogen as a fuel source, hydrogen has not found its place as a mainstream transportation fuel. The major setback for the use of hydrogen appears to be the same properties that make it attractive as a fuel source. Hydrogen is a highly flammable gas whose reaction with oxygen releases a great deal of energy. Any uncontrolled reaction of hydrogen with oxygen is, therefore, invariably explosive. Storage of sufficient amounts of hydrogen in a vehicle to power it for a standard trip on a tank-full of fuel, approximately 300 miles, puts the occupants of the vehicle in a precariously dangerous position if the vehicle encountered an accident that would cause the hydrogen tank to rupture. This tragedy was witnessed when the space shuttle Challenger exploded over the Atlantic Ocean in 1986.

The solution to the above problem appears to be the in situ generation of hydrogen from sources that can provide large quantities of hydrogen on demand, while in themselves do not react uncontrollably with oxygen. The hydrogen source, and the by-products of hydrogen generation, should both be easily disposable and environmentally friendly.

SUMMARY OF THE INVENTION

Disclosed herein are methods of producing molecular hydrogen, where the methods comprise contacting a solution comprising urea with a urease to produce ammonia, and contacting the ammonia with a first catalyst to produce a first gaseous mixture comprising molecular hydrogen.

Also disclosed are methods of producing molecular hydrogen, where the methods comprise contacting a solution comprising urea with a urease to produce ammonia; contacting the ammonia with a first catalyst to produce a first gaseous mixture comprising molecular hydrogen; and contacting the first gaseous mixture with a second catalyst to produce a second gaseous mixture, wherein the second gaseous mixture has a higher percent composition of hydrogen than the first gaseous mixture.

BRIEF DESCRIPTION OF THE DRAWINGS

It will be appreciated that the drawings are not necessarily to scale, with emphasis instead being placed on illustrating the various aspects and features of embodiments of the invention, in which.

DETAILED DESCRIPTION OF THE PREFERRED EMBODIMENTS

Figure 1:
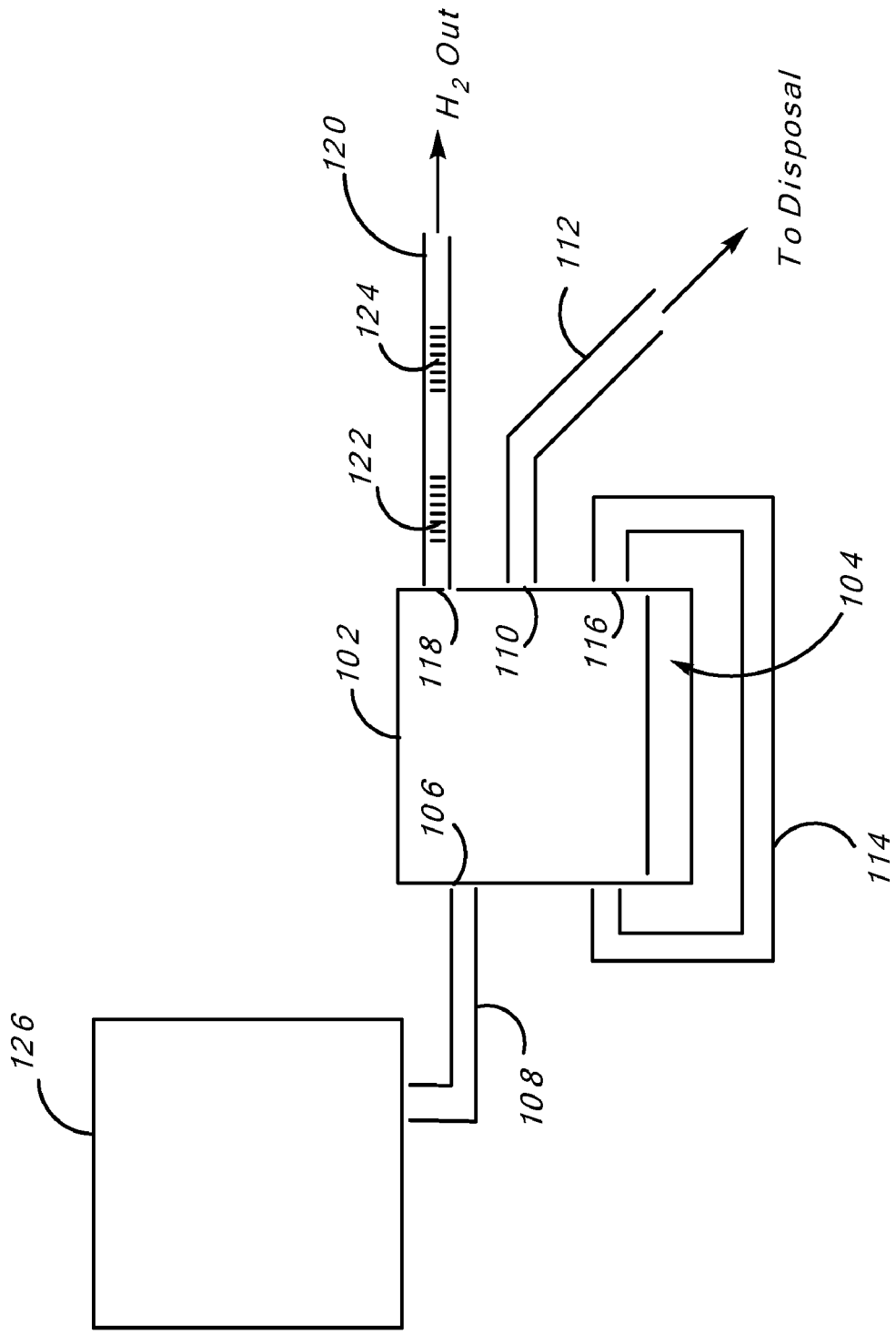
FIG. 1 is an illustration of an embodiment of a hydrogen generator.

In certain aspects, disclosed herein are methods of generating hydrogen from ammonia. The ammonia feedstock can in turn be produced by reacting urease enzymes with urea. Ureases are a well-known class of enzymes that are found in bacteria, several species of yeast, and a number of higher plants. Primarily, ureases catalyze the hydrolysis of urea to form carbon dioxide and ammonia. In some embodiments, the resulting ammonia is present in the solution as ammonium hydroxide. Ammonium hydroxide exists in equilibrium with ammonia, which can be dissolved as a molecular species in the solution. The dissolved ammonia is in turn in equilibrium with gaseous ammonia present in the space over the solution. Therefore, the ammonia produced by the reaction of urease with urea can ultimately be present in gaseous form in the space above the solution containing the reaction mixture.

The Haber Process for the generation of ammonia from hydrogen and nitrogen has been known since the time of World War I. The reaction of the Haber Process is an equilibrium. Through the use of catalysts and the removal of the ammonia from the reaction medium the equilibrium can be pushed in the forward direction to continue the generation of ammonia.

The reverse of the Haber Process, the reaction shown below, can also take place.

$$2NH_3 \rightleftharpoons N_2 + 3H_2$$

That is, with the selection of a right catalyst and optimized reaction conditions, ammonia can be turned to molecular hydrogen and molecular nitrogen. The present inventors have discovered that certain transition metal catalysts are uniquely suited to efficiently catalyze the reverse of the Haber Process. In particular, in some embodiments, the gaseous from of ammonia can be passed over or through catalysts containing nickel to convert the ammonia to hydrogen and nitrogen.

As the stoichiometry of the Reverse Haber Process shows, three moles of hydrogen and one mole of nitrogen are produced for each two moles of ammonia. Therefore, the gas produced by this process is theoretically 75% hydrogen and 25% nitrogen. In actuality, the percentages are less because water vapor from the urea-urease solution and carbon dioxide from the step generating the ammonia are also present in the gas mixture. Also, any other impurities with sufficiently low vapor pressure present in the solution can also be present in the gas mixture produced by the reaction.

In some embodiments, it is desirable to increase the percentage of hydrogen present in the sample. Certain scrubs are commercially available that can remove carbon dioxide and water from the gas mixture. For example, molecular sieves can be used to remove water from the gas mixture. Lithium hydroxide monohydrate can be used to remove carbon dioxide from the mixture. Lithium hydroxide (LiOH) reacts with water to give lithium hydroxide monohydrate ($LiOH.H_2O$), which further reacts with carbon dioxide ($CO_2$) to give lithium carbonate ($Li_2CO_3$) and three equivalents of water. The resulting water can be removed using the molecular sieves.

The remaining main impurity to remove is nitrogen. The present inventors have discovered that a metal catalyst containing lithium can be used to remove nitrogen. Lithium reacts with nitrogen to form lithium nitride, $Li_3N$. In fact, lithium metal appears to be the only Group I metal to undergo such reaction. In some embodiments, the nitrogen can be removed using a mesoporous oxide material, such as SBA 15. These materials have high surface area and absorb nitrogen well.

The hydrogen generated by the methods disclosed herein can be used to create pure elemental hydrogen that can be stored and sold, or used wherever hydrogen is used. Alternatively, the hydrogen can be used as fuel to power a fuel cell or a combustion engine.

Thus, in one aspect, disclosed herein is a method of producing molecular hydrogen, the method comprising contacting a solution comprising urea with a urease to produce ammonia; and contacting the ammonia with a first catalyst to produce a first gaseous mixture comprising molecular hydrogen.

The solution comprising urea comprises a solvent that can dissolve urea or make a suspension thereof so that it can react with a urease. In certain embodiments, the solvent used is an organic solvent. In some embodiments, the solution comprising urea is an aqueous solution. In certain embodiments, the solution comprising urea comprises animal waste, which can optionally be animal urine. Any animal waste that comprises urea can be used as feedstock for the methods described herein. In certain embodiments, the animal is a mammal, which can be selected from the group consisting of mouse, rat, rabbit, guinea pig, dog, cat, sheep, goat, cow, monkey, chimpanzee, ape, and human.

Urease is active through a wide temperature range. However, it is most efficient as a catalyst within an optimized temperature range. Therefore, it is desirable to keep the temperature of the solution comprising the urea and the urease at the optimized temperature range. In some embodiments, the temperature is changed before the solution is contacted with urease. In alternative embodiments, the temperature is changed after the solution is contacted with urease. In some embodiments, the solution comprising urea is warmer than the desired temperature. In these embodiments, the solution is cooled to the desired temperature. In other embodiments, the solution is at below ambient temperature. In these embodiments the solution is heated to the desired temperature.

In some embodiments, the temperature of the solution comprising urea is changed to above 25° C. In some embodiments, the temperature of the solution comprising urea is changed to above 30° C. In some embodiments, the temperature of the solution comprising urea is changed to above 40° C. In some embodiments, the temperature of the solution comprising urea is changed to above 50° C. In some embodiments, the temperature of the solution comprising urea is changed to above 60° C. In some embodiments, the temperature of the solution comprising urea is changed to above 70° C. In some embodiments, the temperature of the solution comprising urea is changed to above 80° C. In some embodiments, the temperature of the solution comprising urea is changed to 69° C.

In some embodiments, the temperature of the solution comprising urea is within a temperature range. In some embodiments, the temperature is between 25-90° C. In other embodiments, the temperature is between 30-80° C. In other embodiments, the temperature is between 40-75° C. In some embodiments, the temperature is between 50-70° C. In some embodiments, the temperature is between 60-70° C.

In some embodiments, the first catalyst comprises a metal, which can be in its elemental form. Alternatively, the metal can be in an oxidation state other than zero, such as in an oxidized state or in reduced state. In some embodiments, the metal catalyst is a main group metal, while in other embodiments, the metal catalyst is a transition metal. In certain embodiments, the transition metal is nickel. In other embodiments, the transition metal is rubidium.

In some embodiments the metal is present as a strip of metal. In other embodiments, the metal is in a salt or compound form and is present in a solid matrix, such as a crystal form. In some embodiments, the metal (whether elemental or otherwise) is present in a ceramic, clay, or other solid state matrix, which is sufficiently porous to allow gaseous ammonia to come in contact with the metal. In other embodiments, the metal (whether elemental or otherwise) is present in a polymer or a gel. In some embodiments, the nickel is present in a mesoporous oxide material, such as SBA 15, which both hold the nickel atoms and is porous to nitrogen.

In additional embodiments, the metal is in the form of a series of semi-porous concentric rings that would allow the gas to pass over the metal more efficiently. The concentric rings present a greater surface area for a more efficient reaction between the metal and the gas. In addition, because the rings somewhat block the flow of gas, they cause a pressure barrier to exist between the upstream space and the downstream space from the ring, which, as explained more fully below, assist in the flow of the gas through the metal catalyst.

In another embodiment, the metal is in the form of powder, or small pellets, which present a high surface area for an efficient reaction to take place. The powder can be used to create a plog flow reaction, as explained below.

In some embodiments, the methods described herein further comprise contacting the first gaseous mixture with a second catalyst to produce a second gaseous mixture, where the second gaseous mixture has a higher percent composition of hydrogen than the first gaseous mixture.

In some embodiments, the second catalyst comprises a metal, which can be in its elemental form. Alternatively, the metal can be in an oxidation state other than zero, such as in an oxidized state or in reduced state. In some embodiments, the metal catalyst is a main group metal, while in other embodiments, the metal catalyst is a transition metal. In certain embodiments, the main group metal is lithium. In some embodiments, the metal is present in a salt form. An example of such salt is LiOH.

In some embodiments, the methods described herein further comprise removing the urease from the solution comprising urea subsequent to producing the first gaseous mixture.

In another aspect, disclosed herein is a method of producing molecular hydrogen, the method comprising contacting a solution comprising urea with a urease to produce ammonia; contacting the ammonia with a first catalyst to produce a first gaseous mixture comprising molecular hydrogen; and contacting the first gaseous mixture with a second catalyst to produce a second gaseous mixture, wherein the second gaseous mixture has a higher percent composition of hydrogen than the first gaseous mixture.

In another aspect, disclosed herein is a device for the generation of hydrogen. FIG. 1 is a schematic drawing of an embodiment of the hydrogen generator 100. The hydrogen generator 100 includes a reaction vessel 102 where the solution comprising urea and the urease are mixed and ammonia is produced.

In some embodiments, the reaction vessel 102 comprises a temperature control unit (not shown). The temperature control unit can raise or lower the temperature of the contents of the reaction vessel 102 or maintain the temperature at a preset value. The temperature control unit may include a jacket around the reaction vessel 102 whereby a cooled or heated fluid is passed through the jacket in order to maintain the temperature of the intraluminal space at a certain predetermined level. Alternatively, the temperature control unit can be a heating element located within the reaction vessel 102 that can heat up the contents thereof.

Alternatively, the reaction vessel 102 does not have a temperature control unit. In these embodiments, the temperature of the solution comprising urea is changed to the predetermined value before the solution is introduced into the reaction vessel 102.

In some embodiments, the urease enzyme is added to the reaction vessel 102 either in solid form or as part of a solution. In other embodiments, the reaction vessel 102 comprises a layer of urease 104. While in FIG. 1 the layer of urease 104 is shown to be located at the bottom of the reaction vessel 102, it is understood that the layer of urease 104 can be located anywhere in the reaction vessel 102, for example attached to one of the walls, located at the center of the vessel 102, or floating therein.

In some embodiments, urease is held in small packets within the layer 104 and is release slowly into the reaction solution. In other embodiments, the layer 104 comprises a controlled release formulation of urease, for example by embedding the urease into a polymer matrix that dissolves at a desired rate.

In some embodiments reaction vessel 102 further comprises a mixer (not shown). The mixer can be a mechanical mixer, a static mixer, or a mechanical agitator such as a rotating blade. Alternatively, the mixer can be a pump that moves the solution around within the reaction vessel 102. In some embodiments, the reaction vessel 102 does not comprise a mixer. In some of these embodiments, the solution agitation caused by the reaction and the generation of gaseous ammonia is sufficient to mix the solution to a satisfactory level.

Preferably, the reaction vessel 102 comprises an opening 106 through which the solution comprising urea is introduced into the vessel 102. In some embodiments, a pipe 108 leads to the opening 106, where the solution comprising urea travels through the pipe 108 and enters the vessel 102 through the opening 106. In some embodiments, the pipe 108 comprises a temperature control unit (not shown) that can raise or lower the temperature of the solution comprising urea before the solution is introduced into the reaction vessel 102. The temperature control unit may include a jacket around the pipe 108 whereby a cooled or heated fluid is passed through the jacket in order to maintain the temperature of the intraluminal space at a certain predetermined level. In other embodiments, the temperature control unit is an electrical coil, or a heating unit, located within lumen of pipe 108 and can heat the liquid that passes through the pipe 108 to the desired temperature.

In some embodiments, the reaction vessel 102 comprises an opening 110 through which the spent reaction mixture leaves the reaction vessel 102. In some embodiments, a pipe 112 leads away from the opening 108. The pipe 112 can lead to a disposal tank, a disposal facility, or the sewer, where the spent reaction mixture is disposed.

At times, the reaction between urease and urea does not go to completion. In other words, after the reaction has proceeded to a point where no appreciable amounts of ammonia are generated anymore, there is still significant amount of urea left in the reaction mixture. It is desirable to re-route the spent reaction mixture (i.e., the reaction mixture after the reaction to generate ammonia has taken place) back into the reaction vessel 102 so that the remaining urea contained therein can be further exposed to the urease. Accordingly, in some embodiments, a feedback loop pipe 114 is provided that can loop the spent reaction mixture back into the reaction vessel 102. In some embodiments, the exit opening 116 (opening through which the spent reaction mixture leaves the reaction vessel 102 and enters the pipe 114) is fit with a filter that can remove urease from the spent reaction mixture and keep the urease within the reaction vessel 102 for further reaction. In some embodiments, the filter is a semi-permeable membrane, which is impermeable towards urease, but is permeable towards smaller molecules, such as water and urea. In some embodiments, a pump (not shown) is provided that can control the flow of liquid through the pipe 114.

An opening 118 is provided through which the generated gaseous ammonia exits the reaction vessel 102. Preferably, a pipe 120 carries the generated gasses downstream.

In some embodiments, embedded within pipe 120 are a series of catalysts. The first catalyst 122 converts ammonia into hydrogen and nitrogen through the reverse Haber Process reaction discussed above. In some embodiments, the catalyst 122 comprises nickel. In some embodiments, catalyst 122 is a powder present as a plug, or is in the form of concentric rings, either of which is located cross-sectionally within the pipe 120 so that the ammonia passes through the catalyst 122. In other embodiments, catalyst 122 lines the lumen of the pipe 120 so that as the ammonia passes through the pipe 120, the ammonia passes over the catalyst 122 and comes in contact with it.

A second catalyst 124 is provided that can remove some of the non-hydrogen gasses, such as carbon dioxide (generated during the hydrolysis of urea) and nitrogen (generated during the reverse Haber Process reaction). The purpose of catalyst 124 is to increase the percentage of hydrogen in the device output. In some embodiments, the catalyst 124 comprises lithium. In some embodiments, catalyst 124 is a powder present as a plug, or is in the form of concentric rings, either of which is located cross-sectionally within the pipe 120 so that the ammonia passes through the catalyst 124. In other embodiments, catalyst 124 lines the lumen of the pipe 120 so that as the ammonia passes through the pipe 120, the ammonia passes over the catalyst 124 and comes in contact with it.

Ultimately, the pipe 120 carries the device output to the site of use. The site of use may be a storage location, a further purifying station, where all or some of the impurities and adventitious gasses in the device output are removed, or a combustion engine where the hydrogen is burned, and the like.

In some embodiments, gases generated in the reaction vessel 102 are sucked or pushed into pipe 120 using a pump (not shown). In other embodiments, there is no pump. As the reaction proceeds, more ammonia is produced which increases the pressure within the reaction vessel 102. The increased pressure causes the gases to escape through pipe 120. Also, as more solution comprising urea is added to the reaction vessel 102, the headspace volume of the vessel 102 is further reduced, which in turn causes the pressure in the headspace to increase, thereby forcing the gases in the headspace to escape through the opening 118 and pipe 120. In addition, when catalysts 122 or 124 are located cross-sectionally within the pipe 120, either as a plug of powder or as concentric circles, they retard the flow of gas through the pipe 120 and thereby create a pressure gradient across the catalyst 122 or 124, such that the pressure upstream from the catalyst 122 or 124 is greater than the pressure downstream from the catalyst 122 or 124. This pressure gradient results in an increase in the pressure of gas in the reaction vessel 102. The increased gas pressure upstream from the catalysts 122 or 124 allows for the gas to move through pipe 120 and away from the vessel 102 without the need of additional mechanical pumping.

When the hydrolysis of urea takes place, urea is converted to $CO_2$ and $NH_3$, both of which escape the solution as gases. This causes the density of the spent solution to be less than the density of the fresh (i.e., unreacted) solution comprising urea. The spent solution will then generally be near the top of the liquid mixture in the reaction vessel 102, whereas the part of the solution which still has a significant amount of urea tends to be towards the bottom. Therefore, in some embodiments, such as the one shown in FIG. 1, the opening 110 is located near the top of the liquid so that the spent solution can leave the vessel 102 through the opening 110 and leave the unreacted solution in the vessel 102. In some of these embodiments (not shown), the opening 106 is towards the bottom of the vessel 102 so that the unreacted solution enters the vessel 102 at the bottom and pushes the spent solution up towards the opening 110.

In the embodiment shown in FIG. 1, the hydrogen generator 100 comprises a holding vessel 126 for holding the supply of the solution comprising urea for the duration of the reaction. The solution comprising urea leaves the holding vessel 126 through pipe 108 and enters the reaction vessel 102 through the opening 106.

EXAMPLES

The following examples are non-limiting and are only illustrative of some of the embodiments of the invention disclosed herein.

Example 1

Ammonia Production

Ammonia was produced using the following procedure:
Pure urine was placed in a beaker. The temperature of the urine was adjusted to the desired temperature (see Table 1). Once desired temperature was reached, urease was placed in the heated urine. The urease used was from *Canavalia ensiformis* (Jack bean) (CAS Number 9002-13-5; obtained from Sigma-Aldrich, cat. #Fluka 94281) at ~8 units/mg (1 unit corresponds to the amount of enzyme which hydrolyzes 1 µmol urea per minute at pH 8.0 and 25° C.).

A sheet of paper soaked in Nessler's solution was immediately placed over the beaker. The color change from white to brown (scale of white/yellow/light brown/medium brown/dark brown) was noted. Darkness of paper relates to amount of Ammonia created. The results are summarized in Table 1.

TABLE 1

Results of Nessler's Solution Test

| Temperature (° C.) | Color at 30 sec | Color at 1 min | Color at 3 min |
|---|---|---|---|
| 5 | Yellow/white | Yellow/white | Lt brown/yellow |
| 10 | Yellow/white | Yellow/Lt. brown | Lt brown |
| 15 | Yellow | Yellow/Lt brown | Lt brown |
| 20 | Yellow | Lt brown | Med brown |

TABLE 1-continued

Results of Nessler's Solution Test

| Temperature (° C.) | Color at 30 sec | Color at 1 min | Color at 3 min |
|---|---|---|---|
| 25 | Yellow/Lt brown | Lt brown | Med brown |
| 30 | Lt brown | Lt/med brown | Med brown |
| 35 | Lt brown | Lt/med brown | Med brown |
| 40 | Lt brown | Med brown | Med brown |
| 45 | Lt/med brown | Med brown | Med brown |
| 50 | Med brown | Med brown | Dark brown |
| 55 | Med brown | Med/dark brown | Dark brown |
| 60 | Dark brown | Dark brown | Dark brown |
| 65 | Dark brown | Dark brown | Dark brown |
| 70 | Dark brown | Dark brown | Dark brown |
| 75 | Dark/med brown | Dark brown | Dark brown |
| 80 | Med brown | Dark/med brown | Dark brown |
| 85 | Lt/med brown | Med brown | Dark/med brown |

Example 2

Hydrogen Production

After ammonia was produced, it was passed through a catalyst to generate hydrogen and nitrogen. Three different catalysts were tested: nickel, platinum, and rubidium. The results are shown in Table 2.

After the ammonia gas was passed and before it was passed through the catalyst, it was passed through a pipe. The pipe was lined with lithium in order to capture $CO_2$ before passing through catalyst. After the catalyst, the gas was passed through a second pipe also lined with lithium. The second exposure to lithium was designed to capture $N_2$ resulting from the dissociation of ammonia into its elemental components.

A balloon was placed at the end of the pipe to capture the effluent gas. The balloon was tied immediately after gas generation was completed. The diameter of the balloon, in inches, was measured. The balloon was then ignited and the intensity of the resulting explosion was noted. The intensity of the explosion was used as a qualitative measurement technique for the presence or absence, and if present, the amount, of hydrogen production. The results are shown in Table 2.

TABLE 2

Results of Hydrogen Generation Test

| Catalyst | Size of balloon (diameter) | Intensity of explosion |
|---|---|---|
| Nickel | 4.3 in | Large explosion, big boom |
| Platinum | 1.7 in | Slight explosion, no sound, not intense |
| Rubidium | 3.7 in | Large explosion, slightly large boom |

What is claimed is:

1. A method of producing molecular hydrogen, the method comprising:
    contacting a solution comprising urea with a urease to produce ammonia; and
    contacting the ammonia with a first catalyst to produce a first gaseous mixture comprising molecular hydrogen and further comprising contacting the first gaseous mixture with a second catalyst to produce a second gaseous mixture, wherein the second gaseous mixture has a higher per cent composition of hydrogen than the first gaseous mixture.

2. The method of claim 1, wherein the solution comprising urea is an aqueous solution.

3. The method of claim 1, wherein the solution comprising urea comprises animal urine wherein the animal is a mammal.

4. The method of claim 1, wherein the solution comprising urea is heated to above ambient temperature prior to being contacted with urease.

5. The method of claim 4, wherein the solution comprising urea is heated to a temperature selected from the group consisting of above 25° C., above 30° C., above 40° C., above 50° C., above 60° C., above 70° C., and above 80° C.

6. The method of claim 1, wherein the first catalyst comprises metal.

7. The method of claim 6, wherein the solution comprising urea is heated to above 70° C.

8. The method of claim 6, wherein the metal is in elemental form or wherein the metal is in an oxidation state other than zero.

9. The method of claim 7, wherein the metal is a main group metal or a transition metal.

10. The method of claim 9, wherein the transition metal is nickel.

11. The method of claim 1, wherein the first gaseous mixture comprises molecular hydrogen and molecular nitrogen.

12. The method of claim 1, further comprising removing the urease from the solution comprising urea subsequent to producing the first gaseous mixture.

13. A method of producing molecular hydrogen, the method comprising:
    contacting a solution comprising urea with a urease to produce ammonia;
    contacting the ammonia with a nickel catalyst to produce a first gaseous mixture comprising molecular hydrogen; and
    contacting the first gaseous mixture with a lithium catalyst to produce a second gaseous mixture, wherein the second gaseous mixture has a higher percent composition of hydrogen than the first gaseous mixture.

14. The method of claim 13, wherein the second catalyst comprises a metal.

15. The method of claim 14, wherein the metal is in elemental form or wherein the metal is in an oxidation state other than zero.

16. The method of claim 14, wherein the metal is a main group metal or a transition metal.

17. The method of claim 16, wherein the main group metal is lithium.

* * * * *